US011306117B2

(12) United States Patent
Hong et al.

(10) Patent No.: US 11,306,117 B2
(45) Date of Patent: *Apr. 19, 2022

(54) WHITENING COMPOSITION CONTAINING NOVEL QUERCETIN-BASED COMPOUND

(71) Applicant: AMOREPACIFIC CORPORATION, Seoul (KR)

(72) Inventors: Yong-Deog Hong, Yongin-si (KR); Jeong-Kee Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 302 days.

This patent is subject to a terminal disclaimer.

(21) Appl. No.: 16/622,017

(22) PCT Filed: Jun. 11, 2018

(86) PCT No.: PCT/KR2018/006602
§ 371 (c)(1),
(2) Date: Dec. 12, 2019

(87) PCT Pub. No.: WO2018/230906
PCT Pub. Date: Dec. 20, 2018

(65) Prior Publication Data
US 2020/0140474 A1    May 7, 2020

(30) Foreign Application Priority Data
Jun. 12, 2017   (KR) .................. 10-2017-0073265

(51) Int. Cl.
| C07H 17/04 | (2006.01) |
| A61K 36/82 | (2006.01) |
| A61K 8/9789 | (2017.01) |
| A61K 9/00 | (2006.01) |
| A61Q 19/02 | (2006.01) |
| A23L 33/105 | (2016.01) |

(52) U.S. Cl.
CPC ............ *C07H 17/04* (2013.01); *A23L 33/105* (2016.08); *A61K 8/9789* (2017.08); *A61K 9/0019* (2013.01); *A61K 36/82* (2013.01); *A61Q 19/02* (2013.01); *A61K 2236/33* (2013.01)

(58) Field of Classification Search
CPC .. A61K 8/9789; A61K 8/602; A61K 31/7048; A61K 9/0019; A61K 2236/33; A61K 2236/331; A61K 36/82; A23L 2002/00; A23L 2250/032; A23L 2250/0644; A23L 2250/21168; A23L 2250/72; A23L 2250/702; A23L 2250/161; A23L 2250/158; C07H 17/04
USPC ........................................................ 514/27
See application file for complete search history.

(56) References Cited

U.S. PATENT DOCUMENTS

| 4,753,929 A | 6/1988 | Matsumoto et al. |
| 2002/0165169 A1 | 11/2002 | Kim et al. |
| 2006/0088610 A1 | 4/2006 | Vorsa et al. |
| 2012/0100087 A1 | 4/2012 | Chang et al. |

FOREIGN PATENT DOCUMENTS

| JP | 2004-10621 A | 1/2004 |
| JP | 2008-208073 A | 9/2008 |
| JP | 2012-092100 A | 5/2012 |
| KR | 10-0975199 B1 | 8/2010 |
| KR | 10-2012-0061733 A | 6/2012 |
| KR | 10-2013-0131095 A | 12/2013 |
| KR | 10-1418788 B1 | 7/2014 |
| KR | 10-2016-0103655 A | 9/2016 |
| WO | 90/06104 A1 | 6/1990 |
| WO | 2008/026507 A1 | 3/2008 |

OTHER PUBLICATIONS

Jung et al, Saudi Journal of Biological Sciences, 2015, 22(6), 706-713.*
Enos Tangke Arung, et al., "Tyrosinase inhibitory effect of quercetin 4'-O-β-D-glucopyranoside from dried skin of red onion (*Allium cepa*)", Natural Product Research, 2011, vol. 25, No. 3, pp. 256-263.
Atsuko Itoh, et al., "Flavonoid Glycosides from Adina racemosa and Their Inhibitory Activities on Eukaryotic Protein Synthesis", Journal of Natural Products, 2004, vol. 67, No. 3, pp. 427-431.
Hyun Gug Jung, et al., "Quercetin-3-O-β-D-glucopyranosyl-(1→6)-β-D-glucopyranoside suppresses melanin synthesis by augmenting p38 MAPK and CREB signaling pathways and subsequent cAMP down-regulation in murine melanoma cells", Saudi Journal of Biological Sciences, 2015, vol. 22, No. 6, pp. 706-713.
Md. Maniruzzaman Manir, et al., "Tea catechins and flavonoids from the leaves of Camellia sinensis inhibit yeast alcohol dehydrogenase", Bioorganic & Medicinal Chemistry, 2012, vol. 20, No. 7, pp. 2376-2381.
Yuping Tang, et al., "Coumaroyl flavonol glycosides from the leaves of Ginkgo biloba", Phytochemistry, 2001, vol. 58, pp. 1251-1256.
Xi-Feng Teng, et al., "Five New Flavonol Glycosides from the Fresh Flowers of Camellia reticulata", Helvetica Chimica Acta, Jul. 21, 2008, vol. 91, No. 7, pp. 1305-1312.
Lu-Rong Xu, et al., "A new acylated flavonol glycoside from Derris triofoliata" Journal of Asian Natural Products Research, 2006, vol. 8, No. 1-2, pp. 9-13.
G. W. Plumb, et al., "Antioxidant properties of flavonol glycosides from tea", Redox Report, 1999, vol. 4, No. 1-2, pp. 13-16.
Keith R. Price, et al., "Flavonol Glycoside Content and Composition of Tea Infusions Made from Commercially Available Teas and Tea Products", J. Agric. Food Chem., 1998, vol. 46, No. 7, pp. 2517-2522.
Yao Li, et al., "Quercetin, inflammation and immunity", Nutrients, 2016, vol. 8, No. 167, pp. 1-14.

(Continued)

*Primary Examiner* — Ganapathy Krishnan
(74) *Attorney, Agent, or Firm* — Merchant & Gould P.C.

(57) ABSTRACT

The present specification relates to a whitening composition containing a novel quercetin-based compound isolated from post-fermented tea, an isomer thereof, a pharmaceutically acceptable salt thereof, a hydrate thereof, or a solvate thereof, wherein the whitening composition can be widely utilized in fields associated with skin whitening and skin care.

13 Claims, 10 Drawing Sheets

(56) References Cited

OTHER PUBLICATIONS

Sheng-Kuo Hsieh, et al., "Identification of biosynthetic intermediates of teaghrelins and teaghrelin-like compounds in oolong teas, and their molecular docking to the ghrelin receptor", Journal of Food and Drug Analysis, 2015, vol. 23, pp. 660-670.
Wu-Xia Bai, et al., "A Novel Acylated Flavonol Tetraglycoside with Inhibitory Effect on Lipid Accumulation in 3T3-L1 Cells from Lu'an GuaPian Tea and Quantification of Flavonoid Glycosides in Six Major Processing Types of Tea Running title: A Novel Acylated Flavonol Tetraglycoside Against Lipid Accumulation from Lu'an GuaPian Tea", Journal of Agricultural and Food Chemistry, 2017, vol. 65, No. 14, pp. 2999-3005.
Yuan-Hao Lo, et al., "Teaghrelins, Unique Acylated Flavonoid Tetraglycosides in Chin-Shin Oolong Tea, Are Putative Oral Agonists of the Ghrelin Receptor", J. Agric. Food Chem., 2014, vol. 62, pp. 5085-5091.
Zhenzhong Yang, et al., "An ultrafiltration high-performance liquid chromatography coupled with diode array detector and mass spectrometry approach for screening and characterising tyrosinase inhibitors from mulberry leaves", Analytica Chimica Acta, 2012, vol. 719, pp. 87-95.
International Search Report and Written Opinion from International Application No. PCT/KR2018/006602, dated Sep. 28, 2018.
International Search Report and Written Opinion from International Application No. PCT/KR2018/006605, dated Sep. 13, 2018.
International Search Report and Written Opinion from International Application No. PCT/KR2018/006608, dated Sep. 20, 2018.
International Search Report and Written Opinion from International Application No. PCT/KR2018/006609, dated Sep. 14, 2018.
Samdayeon Jeju Tangerine Tea by O'Sulloc-Steepster. https://steepster.com/teas/osulloc/56750-samdayeon-jeju-tangerine. Accessed on Apr. 21, 2021, The consumer comment posted as early as 6 years ago (2015).
Rho et al., "Identification of fermented tea (*Camellia sinensis*) polyphenols and their inhibitory activities against amyloid-beta aggregation", Phytochemistry 160:11-18 (2019).
Itoh et al., "Flavonoid Glycosides from Adina racemosa and Their Inhibitory Activities on Eukaryotic Protein Synthesis", J. Nat. Prod. 2004, 67: 427-431 (2004).
Office Action for Japanese Patent Application No. 2019-564863 (dated Feb. 1, 2022).

* cited by examiner

WHITENING COMPOSITION CONTAINING NOVEL QUERCETIN-BASED COMPOUND

CROSS-REFERENCE TO RELATED APPLICATION

This application is a National Stage Application of International Application No. PCT/KR2018/006602, filed Jun. 11, 2018, which claims benefit of Serial No. 10-2017-0073265, filed Jun. 12, 2017 in the Republic of Korea and which applications are incorporated herein by reference. To the extent appropriate, a claim of priority is made to each of the above disclosed applications.

TECHNICAL FIELD

The present specification relates to a whitening composition containing a novel quercetin-based compound.

BACKGROUND ART

Recently, consumers' interest in whitening is increasing due to the increase of ultraviolet rays caused by environmental pollution or destruction of ozone layer. However, as a large amount of side effects and hypersensitivity reactions have been reported for chemical synthetic cosmetics made of artificial synthetic products, attempts have been actively made to obtain cosmetic raw materials from natural materials. Kojic acids, arbutin or derivatives thereof, which have been identified to date, have not been used as cosmetic raw materials because they have problems in safety or stability or are not very efficient in whitening when blended as cosmetic raw materials. For this reason, studies to find whitening active ingredients in natural products have continued, and as a result, substances that exhibit inhibition of the activity of tyrosinase have been found; however, the problems of stability and the appropriate effective concentration remain to be solved.

On the other hand, green tea is drunk in the tea form of leaf or as a fermented tea in order to feel deeper fragrance. Fermented green tea means that a green tea leaf is subject to oxidation treatment, and includes fermented tea oxidized by an oxidase present in the tea leaf, and post-fermented tea fermented by separate microorganisms, not enzymes presented in the tea leaf. Depending on the degree of fermentation, it can be classified into weakly fermented tea, semi-fermented tea, and fully fermented tea, etc. For example, fermented green tea is called with various names, such as green tea, oolong tea, black tea, puer tea, etc., depending on the type and extent of fermentation.

As compared to a leaf tea, the fermented tea not only has a difference in fragrance, but also has a great difference in the type and content of effective ingredients depending on the specific fermentation process and the type of microorganisms. Since various compounds can be produced and separated as described above, various efforts for isolating and identifying unknown new compounds using green tea have been continued.

CITATION LIST

Patent Literature

Patent Literature 1

Korean Patent No. 10-0975199

SUMMARY OF INVENTION

Technical Problem

In one aspect, the object of the present invention is to use a novel quercetin-based compound derived from a post-fermented tea, for whitening.

Solution to Problem

In one embodiment, the present invention may provide a whitening composition including, as effective ingredients, a compound of following formula 1, an optical isomer thereof, a pharmaceutically acceptable salt thereof, a hydrate thereof, a solvate thereof, or an extract of a post-fermented tea comprising the same:

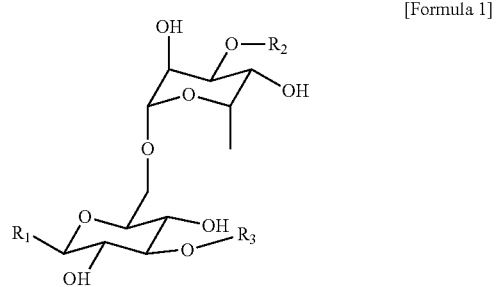

[Formula 1]

wherein in formula 1, $R_1$ is $C_{15}H_9O_7$, $R_2$ is H or $C_6H_{11}O_5$, and $R_3$ is $C_9H_7O_2$. In addition, in another aspect of the present invention, the composition may be a composition for inhibiting one or more of tyrosinase activity and melanogenesis.

According to one embodiment, the present invention provides a method for skin whitening, comprising administering the compound of the formula 1, the optical isomer thereof, the pharmaceutically acceptable salt thereof, the hydrate thereof, the solvate thereof, or the extract of post-fermented tea comprising the same, to a subject in need thereof.

According to one embodiment, the present invention provides a use of the compound of the formula 1, the optical isomer thereof, the pharmaceutically acceptable salt thereof, the hydrate thereof, the solvate thereof, or the extract of post-fermented tea comprising the same in manufacture of a composition for skin whitening.

According to one embodiment, the present invention may provide the compound of the formula 1, the optical isomer thereof, the pharmaceutically acceptable salt thereof, the hydrate thereof, the solvate thereof, or the extract of post-fermented tea comprising the same, for use in skin whitening.

Advantageous Effects of Invention

In one aspect, the present invention enables a novel compound isolated from post-fermented tea to be available in the whitening field, such that the compound can be widely used in the industry associated with post-fermented tea and the field associated with skin care.

EMBODIMENTS

Figure 1:
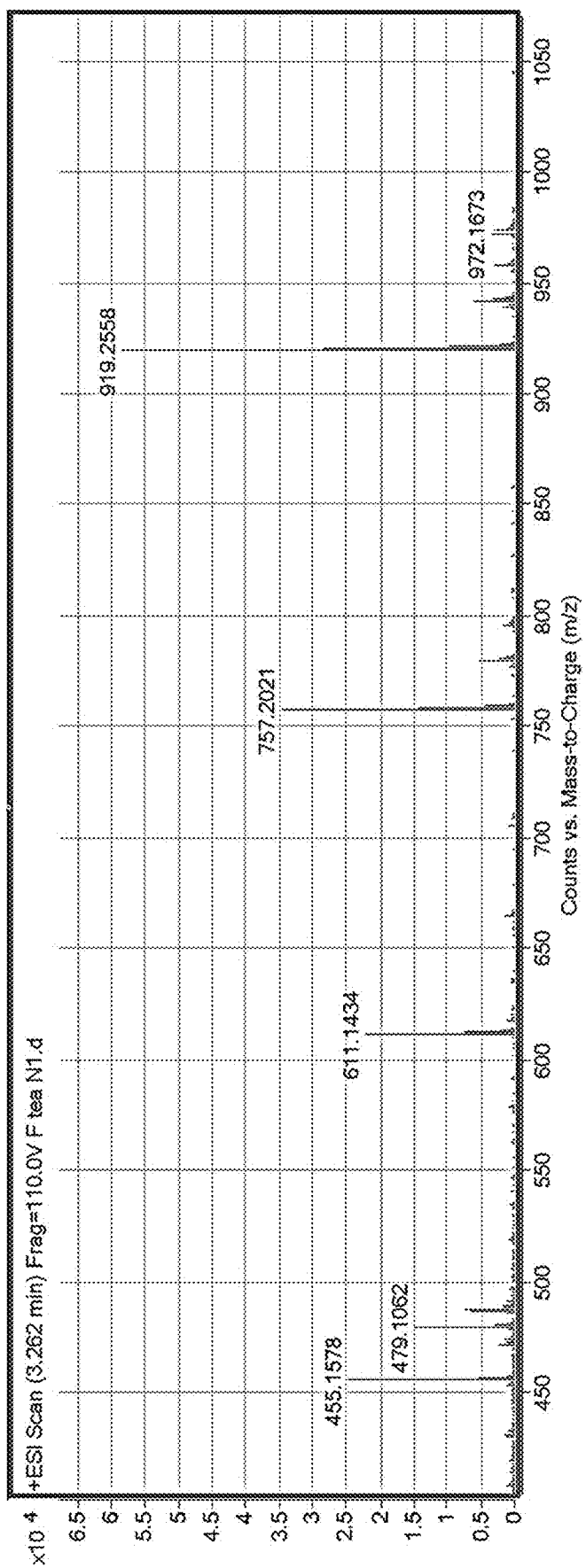
FIG. 1 shows a MS spectrum of Quercetin3-O-[3-O"-(E)-p-coumaroyl][β-D-glucopyranosyl-(1→3)-O-α-L-rhamnopyranosyl-(1→6)-O-β-D-glucopyranoside].

Hereinafter, the present invention will be explained in detail.

In the present specification, the term "post-fermentation" includes fermentation by separate microorganisms or substances, not enzymes present in a tea leaf. Post-fermented tea includes fermented tea according to said process.

In the present specification, the term "extract" includes all substances obtained by extracting ingredients from natural products, regardless of extraction methods or types of ingredients. For example, the extract has the wide range of concept, including all of extracts obtained by extracting ingredients, which can be dissolved in a solvent, from natural products using water or an organic solvent, extracts obtained by extracting particular ingredients, for instance, particular ingredients such as oil, of natural products, fractions obtained by fractionating the extracts obtained therefrom using a certain solvent, etc.

In the present specification, the term "fractions" includes fractions obtained by fractionating a particular substance or extract or the remaining after fractionation using a certain solvent, and extracts obtained by extracting them again using the certain solvent. Any fractionation methods and extraction methods known to a person skilled in the art can be used.

In the present specification, the term "isomers" not only includes, especially, optical isomers (for example, essentially pure enantiomers, essentially pure diastereomers or a mixture thereof), but also includes conformation isomers (that is, isomers wherein one or more chemical bonds are different only in angle), position isomers (especially, tautomers) or geometric isomers (e.g. cis-trans isomers).

In the present specification, the term "essentially pure" means that, for example, when used in connection with enantiomers or diastereomers, the specific compounds such as enantiomers or diastereomers are present in the amount of about 90% or more, preferably about 95% or more, more preferably about 97% or more or about 98% or more, much more preferably about 99% or more, and most preferably about 99.5% or more (w/w).

In the present specification, the term "pharmaceutically acceptable" means that, when used at a typical medicinal dosage, by avoiding significant toxic effects, it can be approved or approved by the government or equivalent regulatory institute for use in animals, more specifically in humans, or recognized as listed in a pharmacopoeia or other general pharmacopeia.

In the present specification, the term "pharmaceutically acceptable salts" means salts according to one aspect of the present invention that are pharmaceutically acceptable and have the desired pharmacological activity of the parent compound. The salts may include (1) acid addition salts that are formed from inorganic acids such as hydrochloric acids, hydrobromic acids, sulfuric acids, nitric acids, phosphoric acids, or the like; or formed from organic acids such as acetic acids, propionic acids, hexanoic acids, cyclopentane-propionic acids, glycolic acids, pyruvic acids, lactic acids, malonic acids, succinic acids, malic acids, maleic acids, fumaric acids, tartaric acids, citric acids, benzoic acids, 3-(4-hydroxybenzoyl) benzoic acids, cinnamic acids, mandelic acids, methanesulfonic acids, ethanesulfonic acids, 1,2-ethane-disulfonic acids, 2-hydroxyethanesulfonic acids, benzenesulfonic acids, 4-chlorobenzenesulfonic acids, 2-naphthalenesulfonic acids, 4-toluenesulfonic acids, camphorsulfonic acids, 4-methylbicyclo [2,2,2]-oct-2-ene-1-carboxylic acids, glucoheptonic acids, 3-phenylpropionic acids, trimethylacetic acids, tert-butylacetic acids, lauryl sulfuric acids, gluconic acids, glutamic acids, hydroxynaphthoic acids, salicylic acids, stearic acids, and muconic acids; or (2) salts formed when acidic protons present in the parent compound are substituted.

In the present specification, the term "hydrate" refers to a compound to which water is bonded, and has a wide range of concept, including inclusion compounds which do not have a chemical bond between water and the compound.

In the present specification, the term "solvate" refers to a higher order compound formed between molecules or ions of a solute and molecules or ions of a solvent.

In one aspect, the present invention provides a skin whitening composition including, as effective ingredients, a compound of following formula 1, an optical isomer thereof, a pharmaceutically acceptable salt thereof, a hydrate thereof, a solvate thereof, or an extract of post-fermented tea comprising the same:

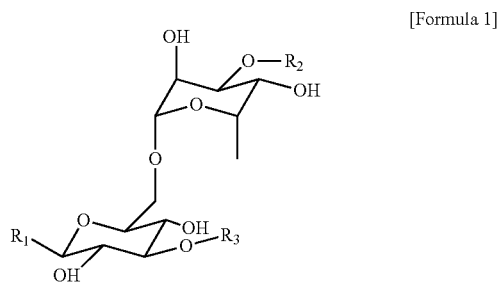

[Formula 1]

wherein in formula 1, $R_1$ may be $C_{15}H_9O_7$, $R_2$ may be H or $C_6H_{11}O_5$, and $R_3$ may be $C_9H_7O_2$.

According to one embodiment, $R_1$ may be a compound of following formula 2:

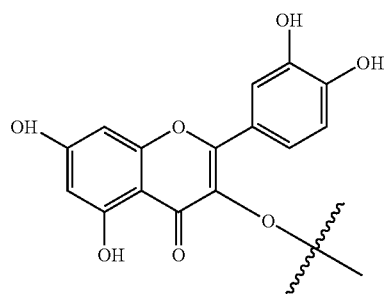

[Formula 2]

According to another embodiment, $R_2$ may be a compound of following formula 3:

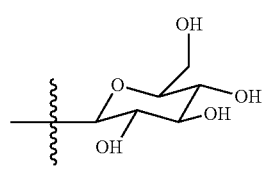

[Formula 3]

$R_3$ may be a compound of following formula 4:

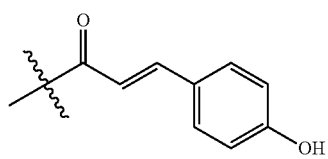

[Formula 4]

According to another embodiment, the compound may be quercetin3-O-[3-O"-(E)-p-coumaroyl][β-D-glucopyranosyl-(1→3)-O-α-L-rhamnopyranosyl-(1→6)-O-β-D-glucopyranoside]. The quercetin3-O-[3-O"-(E)-p-coumaroyl][β-D-glucopyranosyl-(1→3)-O-α-L-rhamnopyranosyl-(1→6)-O-β-D-glucopyranoside] may be represented by following formula 5.

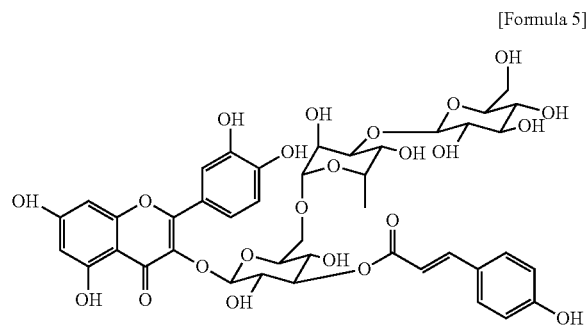 [SMILES: CC1OC(OCC2OC(Oc3c(-c4ccc(O)c(O)c4)oc4cc(O)cc(O)c4c3=O)C(O)C(OC(=O)/C=C/c3ccc(O)cc3)C2O)C(O)C(OC2OC(CO)C(O)C(O)C2O)C1O]

[Formula 5]

According to one another embodiment, the compound may be quercetin3-O-[3-O"-(E)-p-coumaroyl][α-L-rhamnopyranosyl-(1→6)-O-β-D-glucopyranoside]. The quercetin3-O-[3-O"-(E)-p-coumaroyl][α-L-rhamnopyranosyl-(1→6)-O-β-D-glucopyranoside] may be represented by following formula 6.

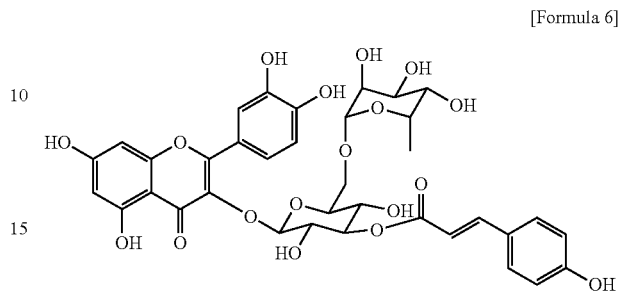

[Formula 6]

According to one aspect of the present invention, a method for preparing the compound, the optical isomer thereof, the pharmaceutically acceptable salt thereof, the hydrate thereof, or the solvate thereof may include synthesis, isolation from natural products, etc.

According to another embodiment, the post-fermentation may be by bacterium inoculation, wherein the strain may be a strain selected from *Saccharomyces* sp., *Bacillus* sp., *Lactobacillus* sp. and *Leuconostoc mesenteroides* sp., and preferably, may be selected from *Saccharomyces cerevisiae, Lactobacillus casei, Bacillus subtlis, Lactobacillus bulgarius* and *Leuconostoc mesenteroides*. According to one another embodiment, the post-fermented tea may be tea obtained by post-fermenting green tea.

In one aspect of the present invention, the compounds were achieved as the result of continuous studies on post-fermented tea by the present inventors, and it was found that the compounds are effective in inhibiting one or more of tyrosinase activity and melanogenesis. Accordingly, the present inventors have proven that the compounds can be used for skin whitening or skin care using said compounds according to one aspect of the present invention (refer to Test Examples 1 and 2).

Melanin is observed in the animal's outer skin, feathers, skin, head, eyes, etc. If melanin is overproduced, it may be deposited on the skin, forming spots, freckles, etc., promoting skin aging, and even causing skin cancer. Diseases or symptoms caused by overproduction of melanin may be one or more selected from the group consisting of freckle, ephelides, liver spot, blemish, epidermal melanocytic lesion, Cafe's au lait macules, birthmark, Becker's Nevus, Nevus Spilus, lentigines, lentigo, dermal melanocytic lesions, Mongolian spot, Nevus of Ota, acquired bilateral nevus of Ota-like macules, Nevus of Ito, Blue nevus, melanocytic nevus, junctional nevus, compound nevus, intradermal nevus, Halo nevus, congenital nevocytic nevus, Spitz nevus, dysplastic nevus, melanoma, lentigo maligna melanoma, superficial spreading melanoma, acral lentiginous melanoma, nodular melanoma, pigment basal cell carcinoma, pigment dermatofibromas, pigment dermoid cyst, pigment keloid, pigmentation (especially, melanin) caused by ultraviolet rays, pigmentation (especially, melanin) caused by drugs, pigmentation (especially, melanin) after inflammation, pigmentation (especially, melanin) occurring in dermatitis, and pigment keratoacanthomas.

The compounds according to one aspect of the present invention are effective in inhibiting one or more of tyrosinase activity and melanogenesis, and thus, the compounds can be used for preventing, treating and improving diseases or symptoms caused by the deposition and overproduction of melanin, etc. (refer to Test Examples 1 and 2).

In one embodiment, the extraction may be an extraction by one or more solvents selected from hot water, a $C_1$ to $C_6$ lower alcohol, and a mixture solvent thereof, and according to another embodiment, the lower alcohol may be an alcohol alone or a mixture that can be typically used in the pertinent art, and preferably, may be ethanol.

According to another aspect of the present invention, the extract may be a fraction obtained by fractionating the extract with ketone after the extraction.

According to another embodiment, the examples of ketones may include acetone, carvon, pulegone, isolongifolanone, 2-heptanone, 2-pentanone, 3-hexanone, 3-heptanone, 4-heptanone, 2-octanone, 3-octanone, 2-nonanone, 3-nonanone, 2-undecanone, 2-tridecanone, methyl isopropyl ketone, ethyl isoamyl ketone, butyliden acetone, methyl heptenone, dimethyl octenone, geranyl acetone, farnesyl acetone, 2,3-pentadione, 2,3-hexadione, 3,4-hexadione, 2,3-heptadione, amylcyclopentanone, amylcyclopentenone, 2-cyclopentyl cyclopentanone, hexylcyclopentanone, 2-n-heptylcyclopentanone, cis-jasmone, dihydrojasmone, methyl corylone, 2-tert-butylcyclohexanone, p-tert-butylcyclohexanone, 2-sec-butylcyclohexanone, celery ketone, krypton, p-tert-pentylcyclohexanone, methyl cyclocitrone, nerone, 4-cyclohexyl-4-methyl-2-pentanone, oxide ketone, emoxy prone, methyl naphthyl ketone, α-methyl anisalacetone, anisylacetone, p-methoxy phenylacetone, benzylidene acetone, p-methoxy acetophenone, p-methylacetophenone, propiophenone, acetophenone, α-dynascone, iritone, ionone, pseudoionone, methylionone, methylylitone, 2,4-di-tert-butylcyclohexanone, allylionone, 2-acetyl-3,3-dimethylnorbornane, verbenone, fenchon, cyclopentadecanone, cyclohexadecenone, etc., and may include all of ketones and a mixture thereof as a solvent that can be typically used in the pertinent art, and preferably, may be acetone.

According to one aspect of the present invention, the content of the compound of formula 1, the optical isomer thereof, the pharmaceutically acceptable salt thereof, the hydrate thereof, or the solvate thereof in the composition may be 0.00001 wt. % to 10 wt. %, relative to the total weight of the composition. The content may be, relative to the total weight of the composition, 0.00001 wt. % or more, 0.00005 wt. % or more, 0.0001 wt. % or more, 0.0005 wt. % or more, 0.001 wt. % or more, 0.005 wt. % or more, 0.01 wt. % or more, 0.05 wt. % or more, 0.1 wt. % or more, 0.5 wt. % or more, 1 wt. % or more, 2 wt. % or more, 3 wt. % or more, 4 wt. % or more, 5 wt. % or more, 6 wt. % or more, 7 wt. % or more, 8 wt. % or more, or 9 wt. % or more. In addition, the amount may be 10 wt. % or less, 9 wt. % or less, 8 wt. % or less, 7 wt. % or less, 6 wt. % or less, 5 wt. % or less, 4 wt. % or less, 3 wt. % or less, 2 wt. % or less, 1 wt. % or less, 0.5 wt. % or less, 0.1 wt. % or less, 0.05 wt. % or less, 0.01 wt. % or less, 0.005 wt. % or less, 0.001 wt. % or less, 0.0005 wt. % or less, 0.0001 wt. % or less, 0.00005 wt. % or less, or 0.00003 wt. % or less.

According to another aspect of the present invention, the content of the extract of post-fermented tea in the composition may be 0.1 wt. % to 90 wt. %, relative to the total weight of the composition. The content may be, relative to the total weight of the composition, 0.1 wt. % or more, 1 wt. % or more, 5 wt. % or more, 10 wt. % or more, 15 wt. % or more, 20 wt. % or more, 25 wt. % or more, 30 wt. % or more, 35 wt. % or more, 40 wt. % or more, 45 wt. % or more, 50 wt. % or more, 55 wt. % or more, 60 wt. % or more, 65 wt. % or more, 70 wt. % or more, 75 wt. % or more, 80 wt. % or more, or 85 wt. % or more. In addition, the amount may be 90 wt. % or less, 85 wt. % or less, 80 wt. % or less, 75 wt. % or less, 70 wt. % or less, 65 wt. % or less, 60 wt. % or less, 55 wt. % or less, 50 wt. % or less, 45 wt. % or less, 40 wt. % or less, 35 wt. % or less, 30 wt. % or less, 25 wt. % or less, 20 wt. % or less, 15 wt. % or less, 10 wt. % or less, 5 wt. % or less, 1 wt. % or less, or 0.5 wt. % or less.

According to one another aspect of the present invention, the extract may comprise the compound of formula 1, the optical isomer thereof, the pharmaceutically acceptable salt thereof, the hydrate thereof, or the solvate thereof in an amount of 0.00001 wt. % or more, 0.00005 wt. % or more, 0.0001 wt. % or more, 0.0005 wt. % or more, 0.001 wt. % or more, 0.005 wt. % or more, 0.01 wt. % or more, 0.05 wt. % or more, 0.1 wt. % or more, 0.5 wt. % or more, 1 wt. % or more, 3 wt. % or more, 5 wt. % or more, 7 wt. % or more, 10 wt. % or more, 12 wt. % or more, 15 wt. % or more, or 18 wt. % or more, on the basis of the total weight of the extract. In another aspect, the extract may comprise them in an amount of 20 wt. % or less, 15 wt. % or less, 12 wt. % or less, 10 wt. % or less, 7 wt. % or less, 5 wt. % or less, 3 wt. % or less, 1 wt. % or less, 0.5 wt. % or less, 0.1 wt. % or less, 0.05 wt. % or less, 0.01 wt. % or less, 0.005 wt. % or less, 0.001 wt. % or less, 0.0005 wt. % or less, 0.0003 wt. % or less, 0.00005 wt. % or less, or 0.00003 wt. % or less. Preferably, the extract may comprise the compound of formula 1, the optical isomer thereof, the pharmaceutically acceptable salt thereof, the hydrate thereof, or the solvate thereof in an amount of 0.00001 wt. % to 20 wt. %, on the basis of the total weight of the extract.

According to one another aspect of the present invention, the dosage of the compound of formula 1, the optical isomer thereof, the pharmaceutically acceptable salt thereof, the hydrate thereof, or the solvate thereof by administering the composition may be 0.00001 mg/kg/day to 100 mg/kg/day. The dosage may be 0.00001 mg/kg/day or more, 0.0001 mg/kg/day or more, 0.001 mg/kg/day or more, 0.005 mg/kg/day or more, 0.01 mg/kg/day or more, 0.05 mg/kg/day or more, 0.1 mg/kg/day or more, 0.5 mg/kg/day or more, 1 mg/kg/day or more, 5 mg/kg/day or more, 10 mg/kg/day or more, 15 mg/kg/day or more, 20 mg/kg/day or more, 25 mg/kg/day or more, 30 mg/kg/day or more, 35 mg/kg/day or more, 40 mg/kg/day or more, 45 mg/kg/day or more, 50 mg/kg/day or more, 55 mg/kg/day or more, 60 mg/kg/day or more, 65 mg/kg/day or more, 7 mg/kg/day or more, 75 mg/kg/day or more, 80 mg/kg/day or more, 85 mg/kg/day or more, 90 mg/kg/day or more, or 95 mg/kg/day or more. In addition, the dosage may be 100 mg/kg/day or less, 95 mg/kg/day or less, 90 mg/kg/day or less, 85 mg/kg/day or less, 80 mg/kg/day or less, 75 mg/kg/day or less, 70 mg/kg/day or less, 65 mg/kg/day or less, 60 mg/kg/day or less, 55 mg/kg/day or less, 50 mg/kg/day or less, 45 mg/kg/day or less, 40 mg/kg/day or less, 35 mg/kg/day or less, 30 mg/kg/day or less, 25 mg/kg/day or less, 20 mg/kg/day or less, 15 mg/kg/day or less, 10 mg/kg/day or less, 5 mg/kg/day or less, 1 mg/kg/day or less, 0.5 mg/kg/day or less, 0.1 mg/kg/day or less, 0.05 mg/kg/day or less, 0.01 mg/kg/day or less, 0.005 mg/kg/day or less, 0.003 mg/kg/day or less, 0.001 mg/kg/day or less, 0.0005 mg/kg/day or less, 0.0001 mg/kg/day or less, or 0.00005 mg/kg/day or less.

According to another aspect of the present invention, the composition may be a food composition, a cosmetic composition, or a pharmaceutical composition.

The food composition according to one aspect of the present invention may be a health food composition, and in the health food composition, the determination of the dosage of the compound can be made at the level of a person skilled in the art, and may vary depending on various factors such as age, health conditions, complications, etc. of the subject to which the composition is administered.

The health food composition according to one aspect of the present invention may be health functional food, and may also include any forms of processed foods, for example, various kinds of foods such as chewing gums, caramels, candies, ice creams, snacks, breads, etc., and beverage products such as soft drink, mineral water, alcoholic drinks, etc., and may be functional foods including vitamin or mineral, etc.

Other than the above, the health food composition according to one aspect of the present invention may include several nutritional supplements, vitamins, minerals (electrolyte), flavoring agents such as synthetic flavoring agents and natural flavoring agents, colorants and enhancers (cheese, chocolate, etc.), pectic acids and salts thereof, alginic acids and salts thereof, organic acids, protective colloid thickeners, pH regulators, stabilizers, preservatives, glycerin, alcohol, carbonation used for carbonated beverages, and the like. In addition, the health food compositions according to one aspect of the present invention may include natural fruit juices and fruit pulps for the preparation of fruit juice drink and vegetable drink. Such ingredients may be used independently or in combination. The ratio of such additives is not important, but the additives are generally comprised in an amount ranging from 0 to about 50 parts by weight per the 100 parts by weight of the composition according to one aspect of the present invention.

The cosmetic composition according to one aspect of the present invention may be, for example, a composition for skin, nail and/or hair, and may have the formulation such as softening lotions, astringent lotions, nourishing lotions, nourishing creams, massage creams, eye creams, eye essence, essence, cleansing creams, cleansing lotions, cleansing foams, cleansing water, packs, powders, body lotions, body creams, body essence, body washing soaps, hair dyes, shampoos, conditioners, hair fixatives, hair-restorers, ointments, gels, creams, patches, aerosols and skin bonding type, etc., but they are not limited thereto.

In addition, in the respective formulations, ingredients, other than the aforementioned essential ingredients, can be suitably selected and blended by a person skilled in the art without any difficulty, depending on types of other external agents or purpose of use.

The cosmetic composition may be provided in all of formulations suitable for local application. For example, the composition may be provided in the formation of, for example, a solution, emulsion obtained by dispersing an oily phase into an aqueous phase, emulsion obtained by dispersing an aqueous phase into an oily phase, suspension, solid, gel, powder, paste, microneedle, foam or aerosol composition. The composition of such formulation may be prepared according to the typical method in the pertinent field.

The cosmetic composition according to the present specification may further include, in addition to the compound, an extract or a fraction of the present specification, functional additives and ingredients that are comprised in general cosmetic compositions. Examples of the functional additives may include ingredient selected from the group consisting of water-soluble vitamins, oil-soluble vitamins, polypeptide, polysaccharide, sphingolipid and plant extracts. The cosmetic composition according to the present specification may preferably include other ingredients which can give synergistic effects to the main effect within the range which does not impair the main effect. In addition, the cosmetic composition according to the present specification may further include a moisturizing agent, an emollient, a surfactant, an ultraviolet absorbent, an antimicrobial agent, a sterilizer, an antioxidant, a pH regulator, organic and inorganic pigments, a flavoring agent, a cooling agent or an antiperspirant agent. The amount of the ingredients blended may be easily selected by a person skilled in the art within the range that does not impair the object and effects of the present specification, and the amount of the ingredients blended may be 0.001 to 10 wt. %, specifically, 0.01 to 3 wt. %, on the basis of the total weight of the composition.

According to one another embodiment, the composition may be a composition for external preparation for skin. The composition for external preparation for skin may be a composition of cosmetics, oral preparations, cleansing agents, pharmaceuticals and preparations for external application for skin, but they are not limited thereto. The formulation of the external preparation for skin is not particularly limited.

In addition, the external preparation for skin in the present specification may further include one or more selected from a functional salt for particular purpose and a pH regulator for pH regulation. Herein, said salt may be selected from an inorganic salt, an organic salt and/or an organic-inorganic salt for ionic shielding, moisturizing, ultraviolet projection, etc. For more detailed examples, said salt can be selected from sodium chloride (NaCl), sodium phosphate (Na3PO4) and calcium chloride (CaCl2), etc. Said pH regulator is selected from acid or base, and may be selected from the group consisting of, for example, hydrochloric acid, sulfuric acid, tartaric acid, citric acid, phosphoric acid, acetic acid, lactic acid, sodium lactate, sodium hydroxide, potassium hydroxide, alkylamine, alkanolamine and ammonia, etc.

The composition for external preparation for skin in the present specification may be a composition of cosmetics, pharmaceuticals and preparations for external application, wherein the composition of cosmetics, pharmaceuticals and preparations for external application may further comprise auxiliaries such as preservatives, stabilizers, hydrating agent or emulsifiers, salts and/or buffers for osmotic pressure control, etc. and other therapeutically useful ingredients. The composition may be in the formulation of lotions, creams, ointments or gels, etc. The composition for external preparation for skin is preferably transdermally administered.

The dosage of the effective ingredients of the composition of pharmaceuticals and preparations for external application may vary depending on age, gender and weight of the subject to which the composition is to be administered, a certain disease or pathology to be treated, severity of the disease or pathology, dosing route and prescriber's decision. The determination of the dosage based on such factors is made at the level of a person skilled in the art. In general, the dosage of the effective ingredient may range from 0.00001 mg/kg/day to 15 mg/kg/day, but this is not limited thereto.

The pharmaceutical composition according to one aspect of the present invention can be administered orally, parenterally, rectally, topically, transdermally, intravenously, intramuscularly, intraperitoneally, subcutaneously, etc. The formulation for the oral administration may be tablets, pills, soft and hard capsules, granules, powders, fine granules, solutions, emulsifying agents or pellets, but they are not limited thereto. The formulation for the parenteral administration may be solutions, suspensions, liquids, gels, injections, drops, suppository, patches or sprays, but they are not limited thereto. The formulations can be easily prepared according to the typical method in the pertinent field, and may further comprise surfactants, excipients, hydrating agent, emulsifiers, suspensions, salts and/or buffers for osmotic pressure control, colorants, perfumes, stabilizers, antimicrobial agents, preservatives, or other commercial auxiliaries.

The amount or dosage of the pharmaceutical composition used according to one aspect of the present invention may vary depending on age, gender and weight, pathology, and its severity of the subject to which the composition is to be administered, dosing route and prescriber's decision. The determination of the dosage based on such factors is made at the level of a person skilled in the art.

The formulation of the food composition is not particular limited, but may be made in, for example, tablets, granules, pills, powders, solutions such as drinks, caramels, gels, bars, tea bags, etc. In the food composition of the respective formulations, in addition to the effective ingredients, ingredients typically used in the pertinent field can be suitably selected and blended by a person skilled in the art without any difficulty, depending on the formulation or purpose of use, and when this composition is applied together with other raw material, a synergistic effect would be generated.

The composition may be administered by various methods, such as simple intake, drinking, injection administration, spray administration, or squeeze administration.

EXAMPLES

Hereinafter, the constitution and effect of the present specification will be explained in more detail with reference to the examples, test examples and formulation examples. However, these examples are provided only for the purpose of the examples in order to help the understanding of the present specification, and the scope and range of the present specification are not limited thereto.

[Example 1] Preparation of Post-Fermented Tea Sample

Water was added to green tea that was made of green tea leaf (*Camellia sinensis* var. *Yabukita*) so as to adjust the moisture content to 40 wt. %. This green tea was inoculated with *Bacillus subtillis* 5×10⁶ cfu/g, and fermented at 50° C. for 3 days and then fermented at 80° C. for 4 days.

The matured tea sample was pulverized for 15 seconds and strained through a stainless sieve of a mesh size 1 mm. Thereafter, 50 mg of the pulverized sample was put into a 1.5 ml Eppendorf tube, and 1 ml of deionized water was added and stirred in a water bath having a constant-temperature of 60° C. at a constant speed for 30 minutes, and then the centrifugation was performed at 25° C. and 13,000 rpm for 15 minutes. Only the portion that was not dissolved in the water was isolated from the extracts of the centrifuged fermented green tea.

[Example 2] Acquisition of Fraction and Isolation of Compound 150 g of the post-fermented tea sample was fractionated with acetone to remove catechin derivatives and caffeine, thereby obtaining a soluble in which other compounds were enriched. For 40 g of the acetone soluble, a fraction was primarily obtained with a solvent of a 5:1 (v/v) mixture of chloroform:methanol, using silica gel column chromatography.

8.9 g of 5:1 (v/v) fraction of chloroform:methanol in which caffeine was removed was fractionated using the high-capacity, high-performance countercurrent chromatography (HPCCC, Dynamic Extractions Ltd, UK). The solvent used herein was n-hexane-TBME (Methyl tert-butyl ether)-BuOH-MeCN-Water (0.25:3:1:1:5, v/v), and the flow velocity was 25 ml/min. The fraction was divided into total 10 subfractions under said conditions, and the ingredients contained in the respective fractions were again isolated using the small-capacity HPCCC (Dynamic Extractions Ltd, UK), HPLC (high-performance liquid chromatography), sephadex LH-20 column (GE Healthcare Bio-Sciences, Sweden), etc.

As the result, quercetin3-O-[3-O''-(E)-p-coumaroyl][β-D-glucopyranosyl-(1→3)-O-α-L-rhamnopyranosyl-(1→6)-O-β-D-glucopyranoside] and quercetin3-O-[3-O''-(E)-p-coumaroyl][α-L-rhamnopyranosyl-(1→6)-O-β-D-glucopyranoside], which are the compounds that have not been known before, could be isolated from the fraction, and the structures of the respective compounds were defined by identifying the structures using $^1$H, $^{13}$C-NMR (nuclear magnetic resonance spectroscopy), UV (ultraviolet spectroscopy), and ESI-MS (Electro Spray Ionization Mass spectroscopy). In the case of $^1$H and $^{13}$C nuclear magnetic resonance (NMR), methanol-d3 was used as the solvent, and Bruker Advance DPX-500 (BRUKER®, USA) was used as the device. The MS spectrums of the respective compounds were analyzed using 6200 Series Accurate-Mass Time-of-Flight (TOF) LC/MS (Agilent, US).

As the analysis result, it was found that the respective compounds were quercetin3-O-[3-O''-(E)-p-coumaroyl][β-D-glucopyranosyl-(1→3)-O-α-L-rhamnopyranosyl-(1→6)-O-β-D-glucopyranoside] having a molecular weight of $C_{42}H_{46}O_{23}$ of 918.2430 ('New Material 31'), and quercetin3-O-[3-O''-(E)-p-coumaroyl][α-L-rhamnopyranosyl-(1→6)-O-α-D-glucopyranoside]having a molecular weight of $C_{36}H_{36}O_{18}$ of 756.1902 ('New Material 32'), which are the compounds that have not been known before.

The formula and NMR data of quercetin3-O-[3-O''-(E)-p-coumaroyl][β-D-glucopyranosyl-(1→3)-O-α-L-rhamnopyranosyl-(1→6)-O-β-D-glucopyranoside] are as below.

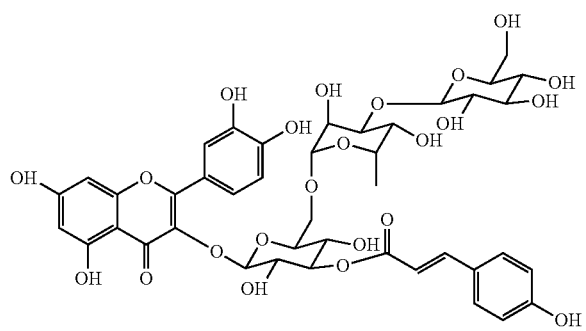 [SMILES: CC1OC(OCC2OC(Oc3c(-c4ccc(O)c(O)c4)oc4cc(O)cc(O)c4c3=O)C(O)C(OC(=O)/C=C/c3ccc(O)cc3)C2O)C(O)C(OC2OC(CO)C(O)C(O)C2O)C1O]

TABLE 1

| Position | $^{13}$C-NMR | $^1$H-NMR |
|---|---|---|
| 2 | 159.29 | |
| 3 | 135.58 | |
| 4 | 179.33 | |
| 5 | 163.02 | |
| 6 | 99.98 | 6.21 (H6, brs) |
| 7 | 166.03 | |
| 8 | 94.95 | 6.41 (H8, brs) |
| 9 | 158.58 | |
| 10 | 105.6 | |

TABLE 1-continued

| Position | $^{13}$C-NMR | $^1$H-NMR |
|---|---|---|
| 1' | 123.06 | |
| 2' | 117.79 | 7.68 (H2', m) |
| 3' | 145.86 | |
| 4' | 149.82 | |
| 5' | 116.13 | 6.86 (H5', d, J = 8.3 Hz) |
| 6' | 123.48 | 7.62 (H6', dd, J = 8.3, 1.3 Hz) |
| p-coumaric acid | | |
| 1''' | 127.3 | |
| 2''', 6''' | 131.18 | 7.48 (H2'''/H6''', d, J = 7.8 Hz) |
| 3''', 5''' | 116.83 | 6.81 (H3'''/H5''', d, J = 7.8 Hz) |
| 4''' | 161.27 | |
| 7''' | 115.45 | 6.42 (H7''', d, J = 15.4 Hz) |
| 8''' | 146.71 | 7.68 (H8''', m) |
| C=O | 168.95 | |
| Glc1 | | |
| 1'' | 104.5 | 5.26 (H1'', d, J = 7.7 Hz) |
| 2'' | 74.11 | 3.71 (H2'', d, J = 9 Hz) |
| 3'' | 78.93 | 5.11 (H3'', t, J = 9 Hz) |
| 4'' | 69.43 | 3.54 (H4'', dd, J = 9.8, 9.3 Hz) |
| 5'' | 77.54 | 3.40 (H5'', m) |
| 6'' | 68.43 | 3.80 (H6'', brd, J = 10.4 Hz) 3.49 |
| Rha | | |
| 1'''' | 102.33 | 4.57 (H1''' ', brs) |
| 2'''' | 70.89 | 3.38 (H2''' ', m) |
| 3'''' | 83.06 | 3.63 (H3''' ', dd, J = 8.9, 2.2 Hz) |
| 4'''' | 72.6 | 3.46 (H4''' ', m) |
| 5'''' | 69.76 | 3.54 (H5''' ', m) |
| 6'''' | 17.96 | 1.10 (H6''' ', d, J = 5.7 Hz) |
| Glc2 | | |
| 1''''' | 105.67 | 4.44 (H1''' '', d, J = 7.5 Hz) |
| 2''''' | 75.48 | 3.25 (H2''' '', m) |
| 3''''' | 76.97 | 3.50 (H3''' '', m) |
| 4''''' | 71.28 | 3.96 (H4''' '', brs) |
| 5''''' | 77.54 | 3.26 (H5''' '', m) |
| 6''''' | 62.1 | 3.78-3.72 (H6''' '', m) |

Figure 2:
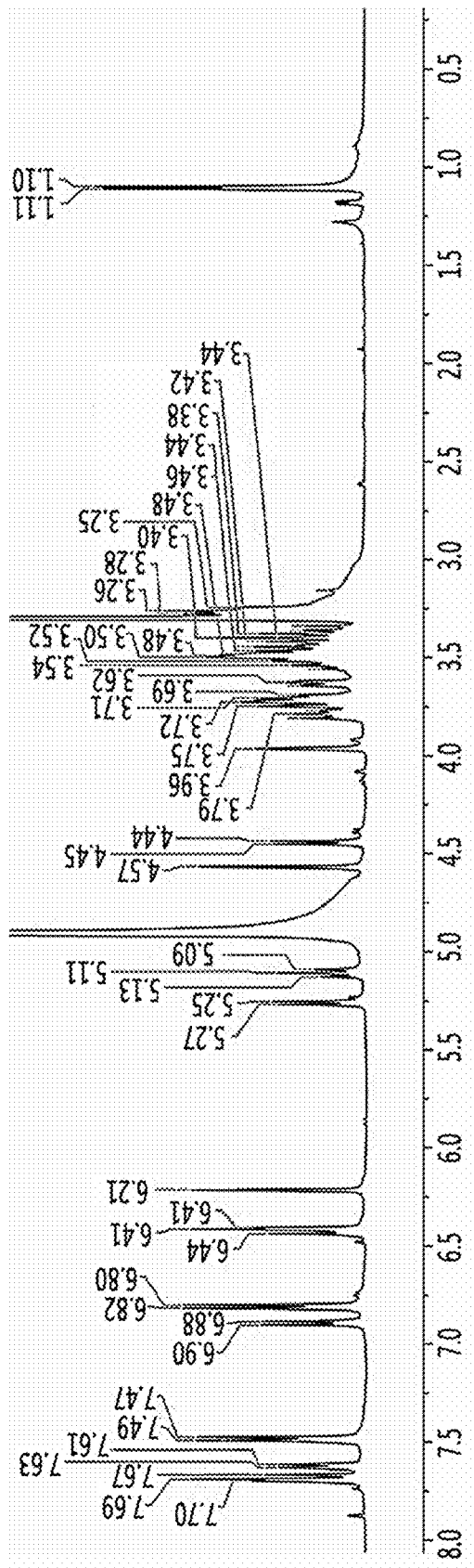
FIG. 2 shows a ¹H-NMR (nuclear magnetic resonance) spectrum of Quercetin3-O-[3-O"-(E)-p-coumaroyl][β-D-glucopyranosyl-(1→3)-O-α-L-rhamnopyranosyl-(1→6)-O-α-D-glucopyranoside].
Figure 3:
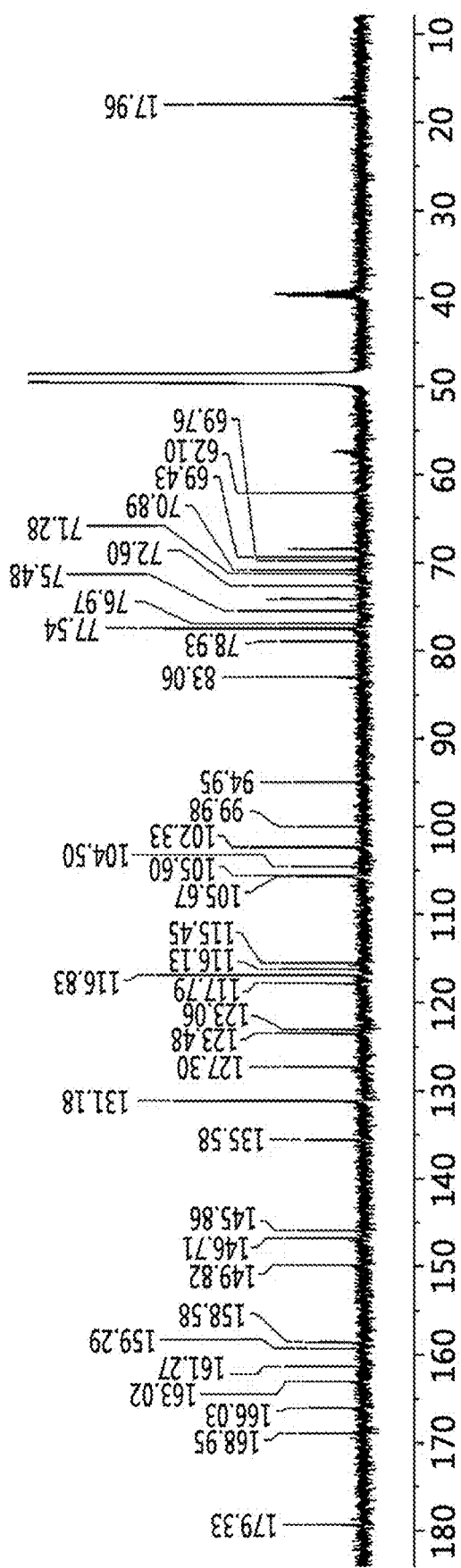
FIG. 3 shows a ¹³C-NMR spectrum of Quercetin3-O-[3-O"-(E)-p-coumaroyl][β-D-glucopyranosyl-(1→3)-O-α-L-rhamnopyranosyl-(1→6)-O-β-D-glucopyranoside].
Figure 4:
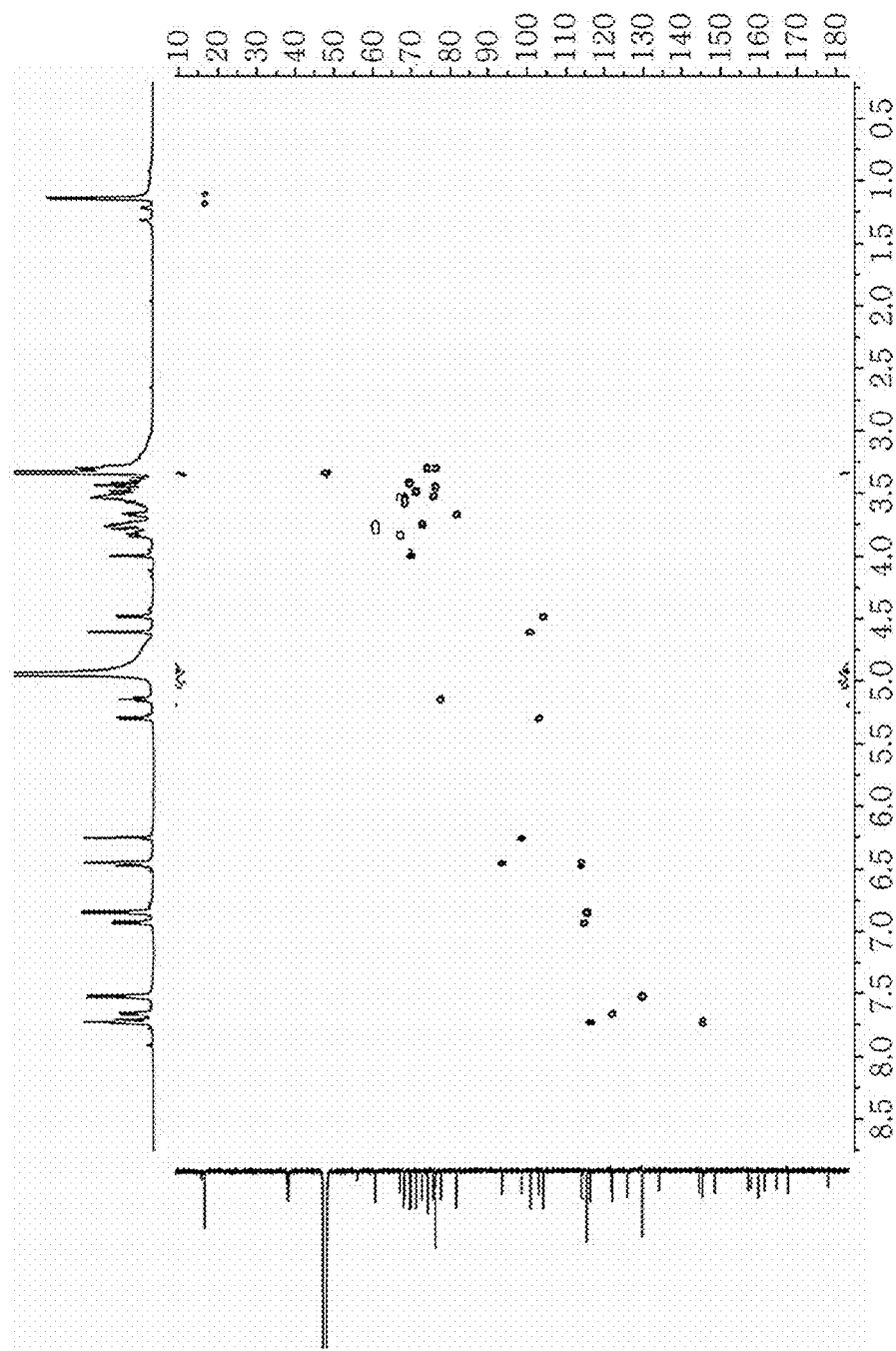
FIG. 4 shows a ¹H-¹³C HSQC (Heteronuclear Single Quantum Coherence) spectrum of Quercetin3-O-[3-O"-(E)-p-coumaroyl][β-D-glucopyranosyl-(1→3)-O-α-L-rhamnopyranosyl-(1→6)-O-β-D-glucopyranoside].
Figure 5:
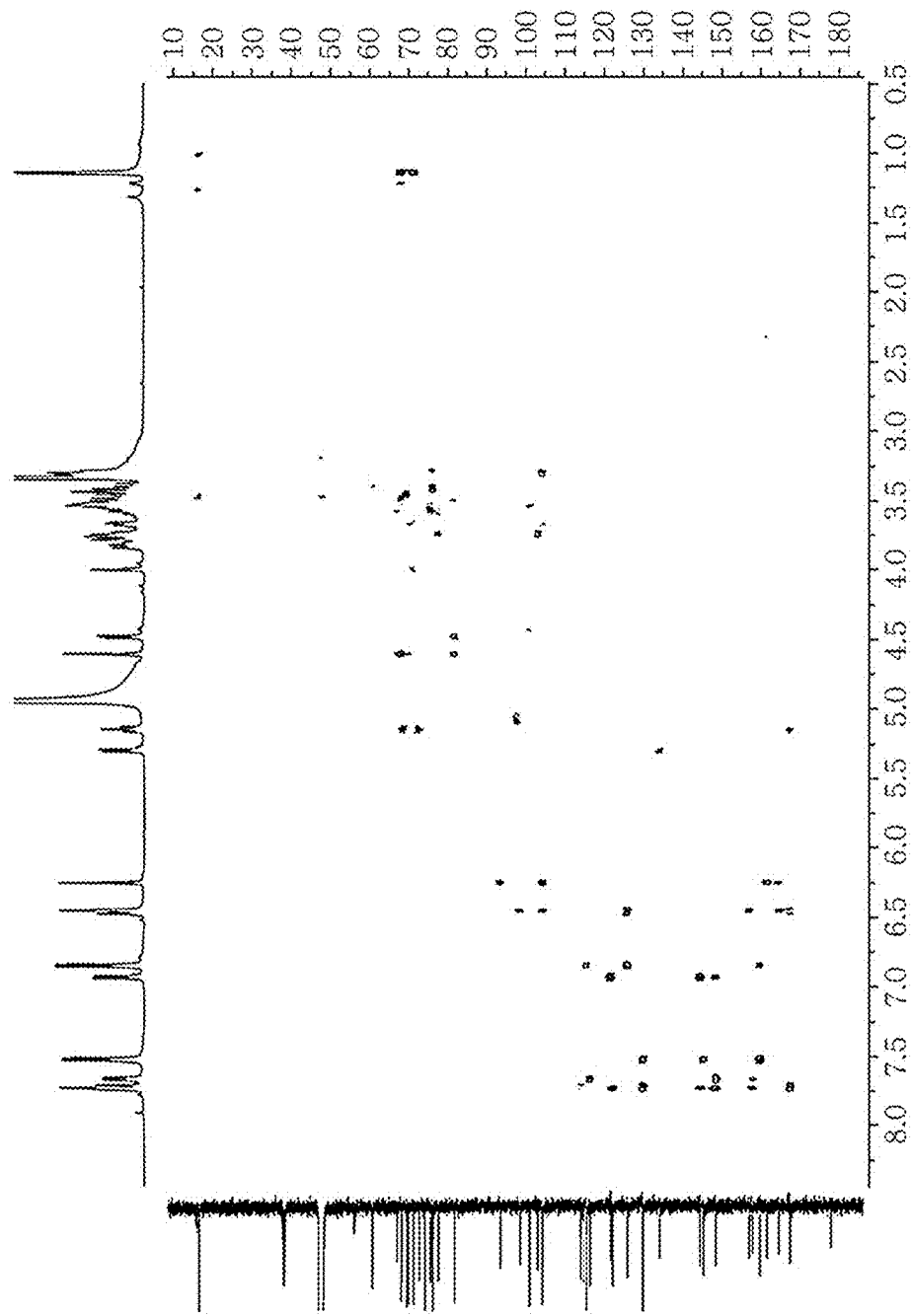
FIG. 5 shows a ¹H-¹³C HMBC (Heteronuclear Multiple-Bond Coherence) spectrum of Quercetin3-O-[3-O"-(E)-p-coumaroyl][β-D-glucopyranosyl-(1→3)-O-α-L-rhamnopyranosyl-(1→6)-O-β-D-glucopyranoside].

MS spectrum of quercetin3-O-[3-O''-(E)-p-coumaroyl][β-D-glucopyranosyl-(1→3)-O-α-L-rhamnopyranosyl-(1→6)-O-β-D-glucopyranoside] was observed as shown in FIG. 1; $^1$H-NMR spectrum and $^{13}$C-NMR spectrum were observed as shown in FIGS. 2 and 3, respectively; HSQC (Heteronuclear Single Quantum Coherence) spectrum was observed as shown in FIG. 4; and HMBC (Heteronuclear Multiple-Bond Coherence) spectrum was observed as shown in FIG. 5.

On the other hand, the formula and NMR data of quercetin3-O-[3-O''-(E)-p-coumaroyl][α-L-rhamnopyranosyl-(1→6)-O-β-D-glucopyranoside] are as below.

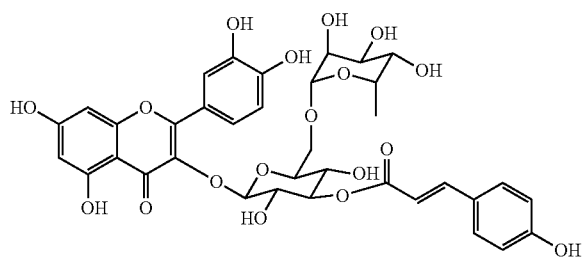 [SMILES: CC1OC(OCC2OC(Oc3c(-c4ccc(O)c(O)c4)oc4cc(O)cc(O)c4c3=O)C(O)C(OC(=O)/C=C/c3ccc(O)cc3)C2O)C(O)C(O)C1O]

TABLE 2

| Position | $^{13}$C-NMR | $^1$H-NMR |
|---|---|---|
| 2 | 159.23 | |
| 3 | 135.52 | |
| 4 | 179.33 | |
| 5 | 163.02 | |
| 6 | 99.96 | 6.21 (H6, brs) |
| 7 | 166.04 | |
| 8 | 94.85 | 6.40 (H8, brs) |
| 9 | 158.52 | |
| 10 | 105.64 | |
| 1' | 123.06 | |
| 2' | 117.68 | 7.67 (H2', d, J = 8.7 Hz) |
| 3' | 145.88 | |
| 4' | 149.86 | |
| 5' | 116.11 | 6.89 (H5', d, J = 8.4 Hz) |
| 6' | 123.52 | 7.63 (H6', dd, J = 8.4, 1.7 Hz) |
| p-coumaric acid | | |
| 1''' | 127.29 | |
| 2''', 6''' | 131.17 | 7.48 (H2'''/H6''', d, J = 8.4 Hz) |
| 3''', 5''' | 116.82 | 6.81 (H3'''/H5''', d, J = 8.4 Hz) |
| 4''' | 161.26 | |
| 7''' | 115.44 | 6.42 (H7''', d, J = 15.7 Hz) |
| 8''' | 146.7 | 7.68 (H8''', d, J = 15.7 Hz) |
| C=O | 168.97 | |
| Glc1 | | |
| 1'' | 101.55 | 5.28 (H1'', d, J = 7.8 Hz) |
| 2'' | 74.14 | 3.71 (2'', d, J = 9 Hz) |
| 3'' | 73.25 | 5.11 (H3'', t, J = 9.2 Hz) |
| 4'' | 70.47 | 3.54 (H4'', dd, J = 9.8, 9.3 Hz) |
| 5'' | 75.51 | 3.40 (H5'', m) |
| 6'' | 67.54 | 3.80 (H6'', brd, J = 10.4 Hz) 3.49 |
| Rha | | |
| 1'''' | 101.85 | 4.53 (H1''' ', brs) |
| 2'''' | 71.34 | 3.38 (H2''' ', m) |
| 3'''' | 83.09 | 3.63 (H3''' ', dd, J = 8.9, 2.2 Hz) |
| 4'''' | 72.6 | 3.46 (H4''' ', m) |
| 5'''' | 69.49 | 3.54 (H5''' ', m) |
| 6'''' | 18.08 | 1.12 (H6''' ', d, J = 6.1 Hz) |

Figure 6:
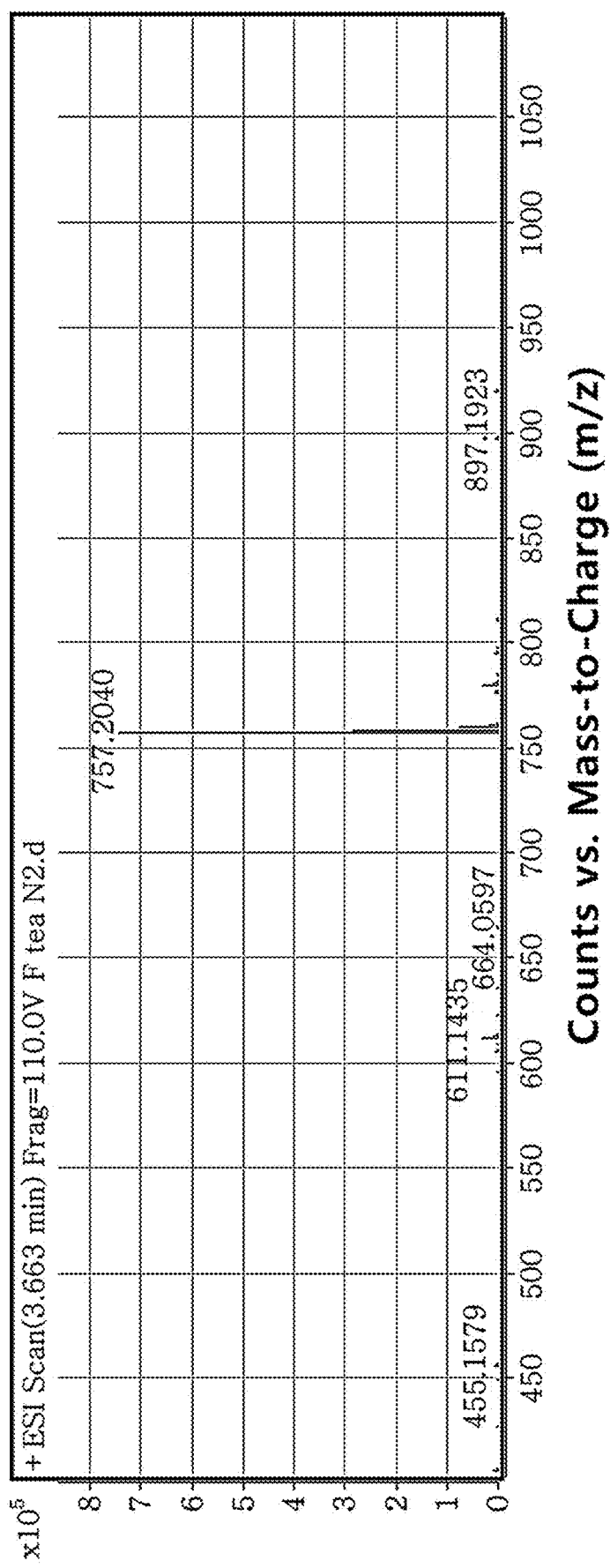
FIG. 6 shows a MS spectrum of quercetin3-O-[3-O"-(E)-p-cumaroyl][α-L-Rhamnopyranosyl-(1→6)-O-α-D-Glucopyranoside].
Figure 7:
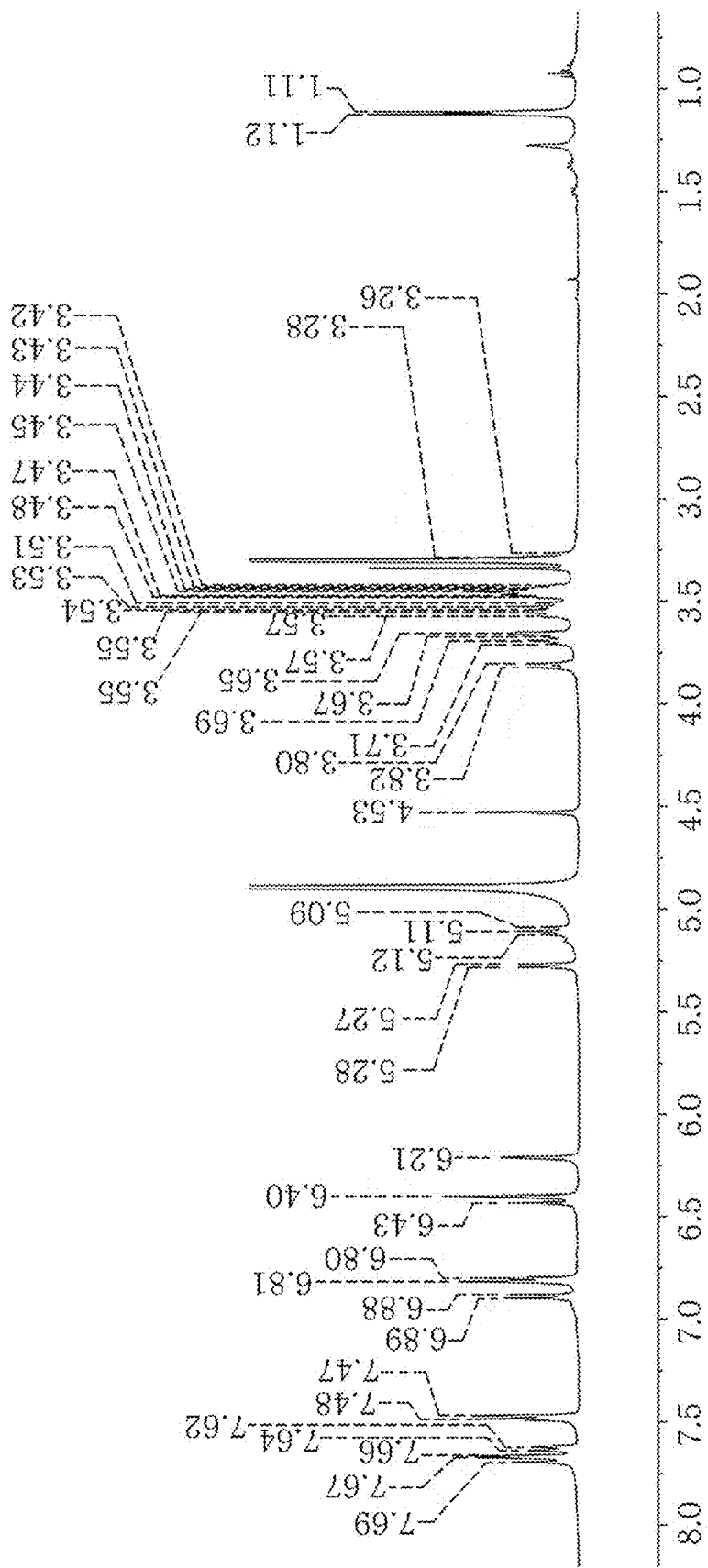
FIG. 7 shows a ¹H-NMR spectrum of quercetin3-O-[3-O"-(E)-p-Cumaroyl][α-L-Rhamnopyranosyl-(1→6)-O-β-D-Glucopyranoside].
Figure 8:
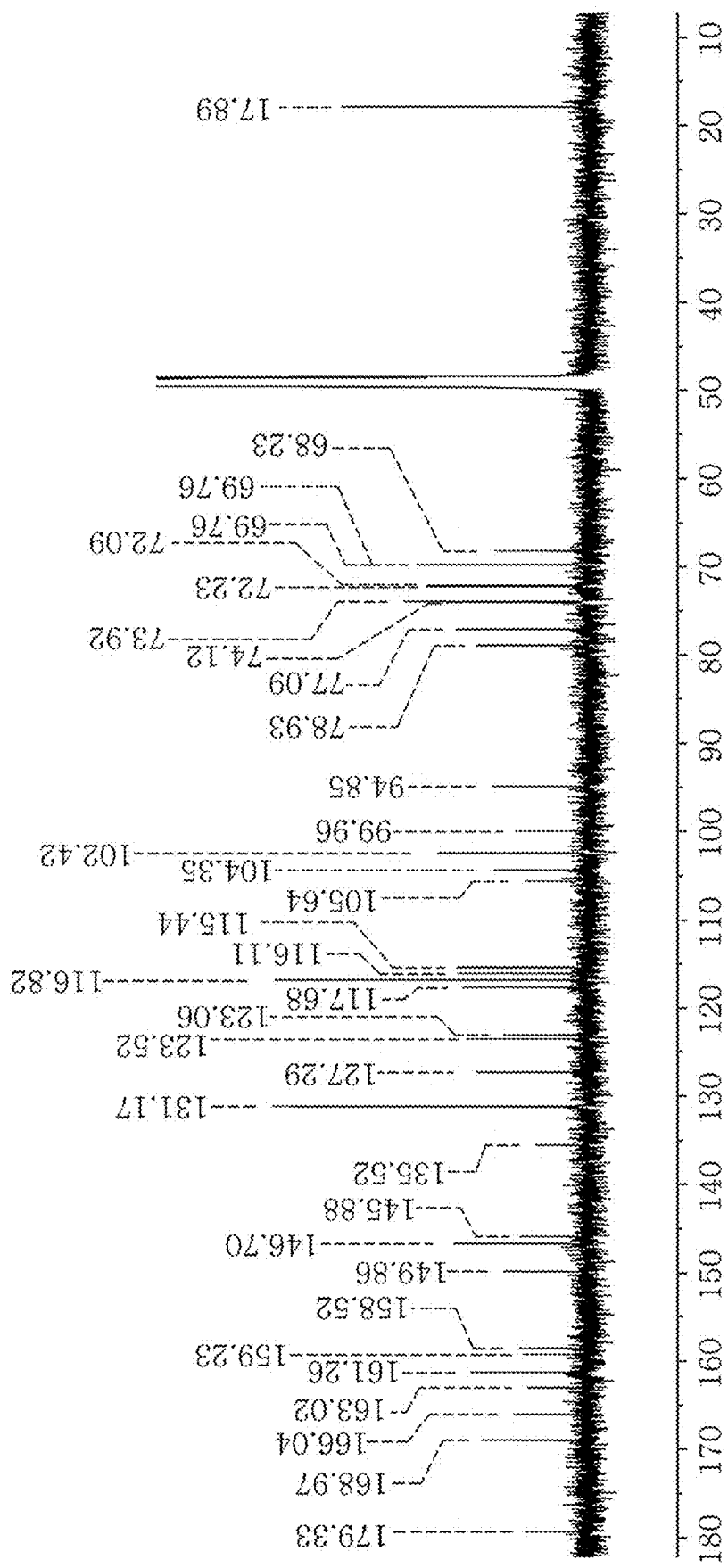
FIG. 8 shows a ¹³C-NMR spectrum of quercetin3-O-[3-O"-(E)-p-Cumaroyl][α-L-Rhamnopyranosyl-(1→6)-O-α-D-Glucopyranoside].
Figure 9:
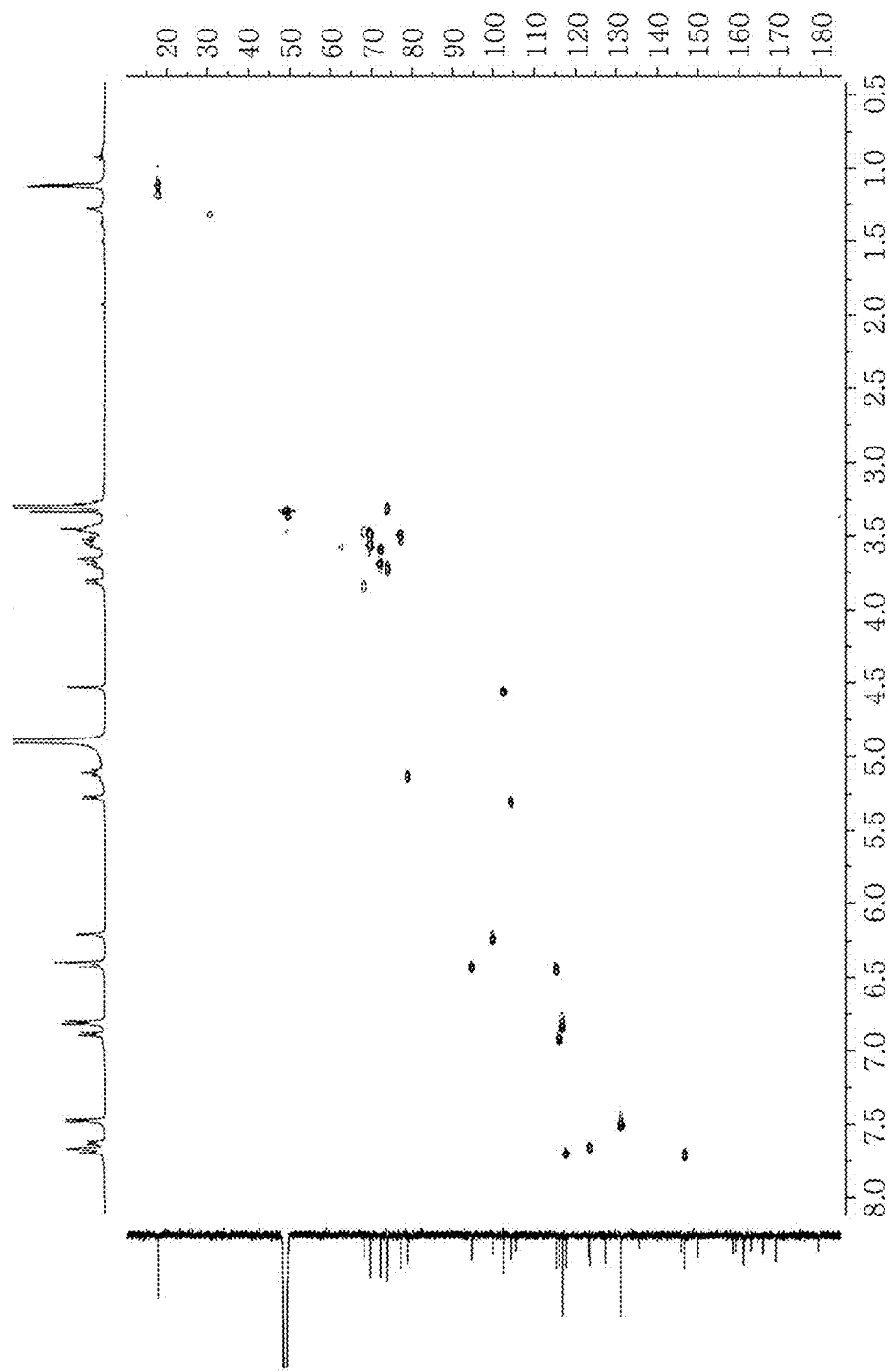
FIG. 9 shows a ¹H-¹³C HSQC (Heteronuclear Single Quantum Coherence) spectrum of quercetin3-O-[3-O"-(E)-p-Cumaroyl][α-L-Rhamnopyranosyl-(1→6)-O-β-D-Glucopyranoside].
Figure 10:
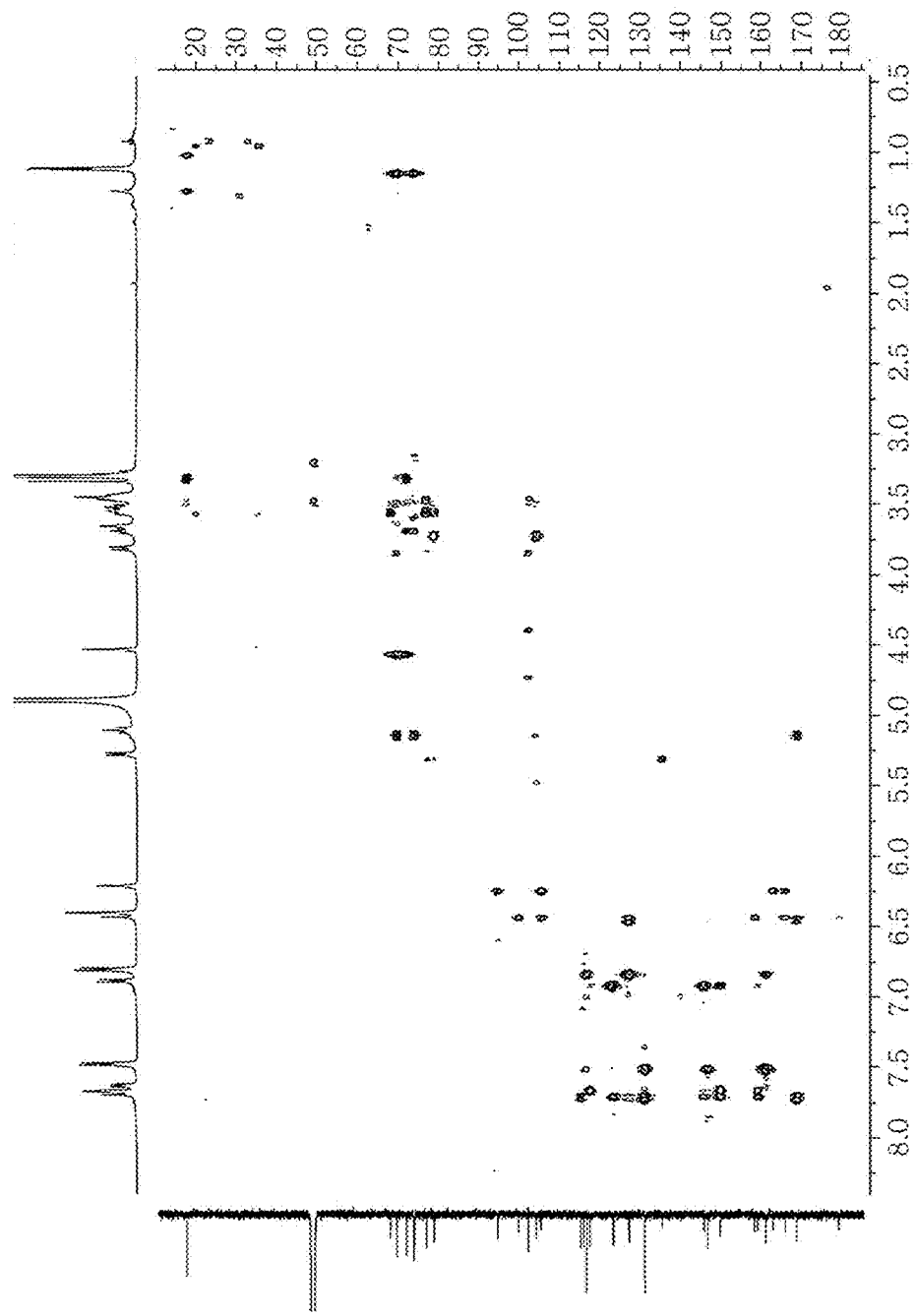
FIG. 10 shows a ¹H-¹³C HMBC (Heteronuclear Multiple-Bond Coherence) spectrum of quercetin3-O-[3-O"-(E)-p-Cumaroyl][α-L-Rhamnopyranosyl-(1→6)-O-β-D-Glucopyranoside].

MS spectrum of quercetin3-O-[3-O''-(E)-p-coumaroyl][α-L-rhamnopyranosyl-(1→6)-O-β-D-glucopyranoside] was observed as shown in FIG. 6; $^1$H-NMR spectrum and $^{13}$C-NMR spectrum were observed as shown in FIGS. 7 and 8, respectively; HSQC (Heteronuclear Single Quantum Coherence) spectrum was observed as shown in FIG. 9; and HMBC (Heteronuclear Multiple-Bond Coherence) spectrum was observed as shown in FIG. 10.

[Test Example 1] Evaluation of the Effect of Inhibiting of Tyrosinase Activity

The effect of New Materials 31 and 32 on inhibiting tyrosinase activity was evaluated.

Specifically, tyrosinase and tyrosine derived from mushroom were obtained from Sigma Chemical. Together with 150 μl of 0.1 M phosphate buffer (pH 6.5), 8 μl of mushroom tyrosinase (2,100 unit/ml) and 0.05 M concentration of L-tyrosine, arbutin and New Materials 31 and 32 were treated at the concentrations of following Table 3, respectively. The tyrosinase activity was evaluated by performing the enzyme reaction at 37° C. for 20 minutes and then measuring absorbance at 490 nm using a microplate reader (Bio-Rad 3550, Richmond, Calif., U.S.A.).

The effects ($IC_{50}$) of New Materials 31 and 32 on inhibiting tyrosinase activity were calculated and shown in Table 3.

TABLE 3

Effects of New Materials on inhibiting tyrosinase activity

| Test Material | IC$_{50}$ (ppm) |
|---|---|
| Control | — |
| 31 | 16 |
| 32 | 19 |
| Arbutin | 149 |

[Test Example 2] Evaluation of the Effect of Inhibiting of Melanogenesis

The effects of New Materials 31 and 32 on inhibiting melanogenesis were compared with Kojic acids which have been known to have an excellent skin whitening effect, and measured.

Specifically, the degree of melanogenesis in cells was measured by a method of Dooley. As the cell line, Mel-Ab cell line (Falcon, U.S.A.) derived from a skin pigment of C57BL/6 was used. Culturing was made under the condition of 37° C., 5% $CO_2$ of a DMEM medium containing 10% placenta serum, 100 nM 12-O-tetradecanoylphorbol-13-acetate, and 1 nM Cholera Toxin. The test materials were treated in the manner where the cultured Mel-Ab cell was isolated with 0.25% trypsin-EDTA, and inoculated again with the same number (1×10$^5$ cells/well) in the 24-well plate, and then the medium was replaced with a medium containing the test materials for two days from the second day. As the test materials, 5 ppm, 10 ppm, 25 ppm and 50 ppm of New Materials 31 and 32, 25 ppm, 50 ppm and 100 ppm of Kojic acids and DMSO (control) were used. After 5 days, the test materials were treated with 1N-NaOH to dissolve melanin contained in the cell, and the amount of melanin was measured by measuring absorbance at 400 nm. The concentration (IC$_{50}$) of the material necessary for reducing melanogenesis of melanocyte by half was calculated, and the results are shown in following Table 4.

TABLE 4

Effects of New Materials on inhibiting melanogenesis

| Test Material | IC$_{50}$ (ppm) |
|---|---|
| Control | — |
| 31 | 23.5 |
| 32 | 23.5 |
| Kojic acids | 39.36 |

[Test Example 3] Test for Skin Accumulated Stimulus

HRIPT (Human repeated insult patch tests) was conducted in order to identify skin accumulated stimulus of quercetin3-O-[3-O''-(E)-p-coumaroyl][β-D-glucopyranosyl-(1→3)-O-α-L-rhamnopyranosyl-(1→6)-O-β-D-glucopyranoside] and quercetin3-O-[3-O''-(E)-p-coumaroyl][α-L-rhamnopyranosyl-(1→6)-O-β-D-glucopyranoside] and to calculate the concentration range that can be used in skin.

Specifically, 15 healthy adult examinees were randomly selected, and test compositions in which the compounds were respectively comprised in an amount of 0.5 wt. %, 1 wt. %, and 3 wt. % (the compositions for skin, comprising an emulsifying agent, a stabilizer, purified water, etc. in addition to the compounds) were dropped in the amount of 20 μl per chamber (IQ chamber, Epitest Ltd, Finland), and patched on the right site of the upper back of the examinees, and then, after 24 hours, the patch was replaced with a new patch. A total of 9 patches were conducted, three times a week for total 3 weeks, in such manner, the skin reactions before and after patch were examined every time, and the skin reactions until 48 hours after removing the final patch were observed, and the average reactivity was observed.

The result is shown in the following Table 5.

TABLE 5

| Test material and content | Number of examinees who exhibited ±, +, or ++ reactivity (unit: number) | | | | | | | | | average reactivity |
|---|---|---|---|---|---|---|---|---|---|---|
| | 1st | 2nd | 3rd | 4th | 5th | 6th | 7th | 8th | 9th | |
| Control | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| New material 31 0.5 wt.% | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| New material 31 1 wt.% | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| New material 31 3 wt.% | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| New material 32 0.5 wt.% | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| New material 32 1 wt.% | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| New material 32 3 wt.% | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |

[[Reactivity]] −: negative (no response) ±: doubtful or slight erythema, etc. +: weak reaction (which is accompanied with no phlyctenule), erythema, papule ++: severe reaction (which is accompanied with phylctenule), erythema, papule, phlyctenule +++: strong reaction, bullae reaction
[[Average reactivity equation]]Average Reactivity = [{total sum of the value obtained by multiplying the number of the examinees who exhibited the reactivity and the reaction index)/(total number of the examinees × highest point (4 point))} × 100]/number of examinations (9 tests) In the equation, if the reactivity is −, the reaction index is 0, if the reactivity is ±, the reaction index is 1, if the reactivity is +, the reaction index is 2, and if the reactivity is ++, the reaction index is 4. When the average reactivity is less than 3, it is considered as a stable composition.

The skin reaction was determined according to the criteria of International Contact Dermatitis Research Group (ICDRG). In the above table, "New Material 31" refers to quercetin3-O-[3-O''-(E)-p-coumaroyl][β-D-glucopyranosyl-(1→3)-O-α-L-rhamnopyranosyl-(1→6)-O-β-D-glucopyranoside], and "New Material 32" refers to quercetin3-O-[3-O''-(E)-p-coumaroyl][α-L-rhamnopyranosyl-(1→6)-O-β-D-glucopyranoside]. In other words, the both materials observed the (−) reactivity (no examinees who exhibited ±, +, ++, or +++ reactivity) within the above range of contents, and from this, it was found that said materials give no skin accumulated stimulus and thus can be stably used for skin.

Hereinafter, the formulation examples of the composition according to one aspect of the present invention will be explained, but the scope of the present invention is not limited thereto.

[Formulation Example 1] Soft Capsule

A soft capsule was prepared by mixing 10 mg quercetin3-O-[3-O''-(E)-p-coumaroyl][β-D-glucopyranosyl-(1→3)-O-α-L-rhamnopyranosyl-(1→6)-O-β-D-glucopyranoside] or quercetin3-O-[3-O''-(E)-p-coumaroyl][α-L-rhamnopyranosyl-(1→6)-O-β-D-glucopyranoside], 80-140 mg L-carnitine, 180 mg soybean, 2 mg palm oil, 8 mg vegetable oil, 4 mg yellow wax and 6 mg lecithin, and filling it in one capsule according to the typical method.

[Formulation Example 2] Tablet

A tablet was prepared by mixing 10 mg quercetin3-O-[3-O"-(E)-p-coumaroyl][β-D-glucopyranosyl-(1→3)-O-α-L-rhamnopyranosyl-(1→6)-O-β-D-glucopyranoside] or quercetin3-O-[3-O"-(E)-p-coumaroyl][α-L-rhamnopyranosyl-(1→6)-O-β-D-glucopyranoside], 200 mg galactooligosaccharide, 60 mg lactose and 140 mg maltose, and granulating it using a fluidized bed drier, and then adding 6 mg sugar ester, and tableting it using a tablet machine.

[Formulation Example 3] Granule

A Granule was prepared by mixing 5 mg quercetin3-O-[3-O"-(E)-p-coumaroyl][β-D-glucopyranosyl-(1→3)-O-α-L-rhamnopyranosyl-(1→6)-O-β-D-glucopyranoside] or quercetin3-O-[3-O"-(E)-p-coumaroyl][α-L-rhamnopyranosyl-(1→6)-O-β-D-glucopyranoside], 250 mg anhydrous crystal glucose and 550 mg starch, and molding it in granules using a fluidized bed granulator, and then filling it in a pouch.

[Formulation Example 4] Drink

A drink was prepared by mixing 2 mg quercetin3-O-[3-O"-(E)-p-coumaroyl][β-D-glucopyranosyl-(1→3)-O-α-L-rhamnopyranosyl-(1→6)-O-β-D-glucopyranoside] or quercetin3-O-[3-O"-(E)-p-coumaroyl][α-L-rhamnopyranosyl-(1→6)-O-β-D-glucopyranoside], 10 g glucose, 0.6 g citric acid and 25 g liquid oligosaccharide, and adding 300 ml purified water and filling 200 ml in each bottle. After filling it in the bottle, the bottle was sterilized for 4-5 seconds at 130° C. to prepare the drink.

[Formulation Example 5] Injection

An injection was prepared using 20 mg quercetin3-O-[3-O"-(E)-p-coumaroyl][β-D-glucopyranosyl-(1→3)-O-α-L-rhamnopyranosyl-(1→6)-O-β-D-glucopyranoside] or quercetin3-O-[3-O"-(E)-p-coumaroyl][α-L-rhamnopyranosyl-(1→6)-O-β-D-glucopyranoside], the proper amount of sterile distilled water for injection, and the proper amount of pH regulator according to the typical method.

[Formulation Example 6] Health Food

Health food was prepared with the composition shown in the following table 6, according to the typical method.

TABLE 6

| Ingredient | amount |
| --- | --- |
| Quercetin3-O-[3-O"-(E)-p-coumaroyl] [β-D-glucopyranosyl-(1→3)-O-α-L-rhamnopyranosyl-(1→6)-O-β-D-glucopyranoside] or quercetin3-O-[3-O"-(E)-p-coumaroyl] [α-L-rhamnopyranosyl-(1→6)-O-β-D-glucopyranoside] | 0.5 mg |
| vitamin mixture | |
| vitamin A acetate | 70 mg |
| vitamin E | 1.0 mg |
| vitamin B1 | 0.13 mg |
| vitamin B2 | 0.15 mg |

TABLE 6-continued

| Ingredient | amount |
| --- | --- |
| vitamin B6 | 0.5 mg |
| vitamin B12 | 0.2 mg |
| vitamin C | 10 mg |
| biotin | 10 mg |
| nicotinic acid amide | 1.7 mg |
| folic acid | 50 mg |
| calcium pantothenate | 0.5 mg |
| inorganic mixture | |
| ferrous sulfate | 1.75 mg |
| zinc oxide | 0.82 mg |
| magnesium carbonate | 25.3 mg |
| potassium dihydrogen phosphate | 15 mg |
| dibasic calcium phosphate | 55 mg |
| potassium citrate | 90 mg |
| calcium carbonate | 100 mg |
| magnesium chloride | 24.8 mg |

The composition ratio of the vitamins and the inorganic mixture is just an example of mixture of the ingredients relatively suitable for health good, and any modifications of the mixing ratio can be made, and said ingredients can be mixed according to the typical method for preparing health food and then used for the preparation of the health food composition according to the typical method.

[Formulation Example 7] Health Beverage

TABLE 7

| Ingredient | amount |
| --- | --- |
| Quercetin3-O-[3-O"-(E)-p-coumaroyl][β-D-glucopyranosyl-(1 → 3)-O-α-L-rhamnopyranosyl-(1 → 6)-O-β-D-glucopyranoside] or Quercetin3-O-[3-O"-(E)-p-coumaroyl][α-L-rhamnopyranosyl-(1 → 6)-O-β-D-glucopyranoside] | 2 mg |
| citric acid | 1000 mg |
| oligosaccharide | 100 g |
| plum concentrate | 2 g |
| taurine | 1 g |
| purified water | balance |
| total volume | 900 Ml |

As shown in the table 6, the balance of purified water was added so that the total volume is 900 ml, and then said ingredients were mixed according to the typical method for preparing health beverage, stirred and heated at 85° C. for about 1 hour, and then, the resulted solution was filtered to a 2 liter of a sterilized container and sealed and sterilized and stored in a refrigerator to prepare health beverage.

[Formulation Example 8] Softening Lotion (Skin Lotion)

A softening lotion (skin lotion) was prepared using 0.2 wt. % quercetin3-O-[3-O"-(E)-p-coumaroyl][β-D-glucopyranosyl-(1→3)-O-α-L-rhamnopyranosyl-(1→6)-O-β-D-glucopyranoside] or quercetin3-O-[3-O"-(E)-p-coumaroyl][α-L-rhamnopyranosyl-(1→6)-O-β-D-glucopyranoside], 1.00 wt. % L-ascorbic acid-2-magnesium phosphate, 5.00 wt. % water-soluble collagen (1% aqueous solution), 0.10 wt. % sodium citrate, 0.05 wt. % citric acid, 0.20 wt. % extract of licorice root, 3.00 wt. % 1,3-butylene glycol, and the balance of purified water.

[Formulation Example 9] Cream Preparation

A cream preparation was prepared using 0.2 wt. % quercetin3-O-[3-O"-(E)-p-coumaroyl][β-D-glucopyranosyl-(1→3)-O-α-L-rhamnopyranosyl-(1→6)-O-β-D-glucopyranoside] or quercetin3-O-[3-O"-(E)-p-coumaroyl][α-L-rhamnopyranosyl-(1→6)-O-β-D-glucopyranoside], 2.00 wt. % polyethylene glycol monostearate, 5.00 wt. % self-emulsifying glycerin monostearate, 4.00 wt. % propylene glycol, 6.00 wt. % squalene, 6.00 wt. % tri2-ethylhexan glyceryl, 1.00 wt. % sphingoglycolipid, 7.00 wt. % 1,3-butylene glycol, 5.00 wt. % beeswax, and the balance of purified water.

[Formulation Example 10] Pack

A composition was prepared using 0.2 wt. % quercetin3-O-[3-O"-(E)-p-coumaroyl][β-D-glucopyranosyl-(1→3)-O-α-L-rhamnopyranosyl-(1→6)-O-β-D-glucopyranoside] or quercetin3-O-[3-O"-(E)-p-coumaroyl][α-L-rhamnopyranosyl-(1→6)-O-β-D-glucopyranoside], 21.00 wt. % polyvinyl alcohol, 3.00 wt. % L-ascorbic acid-2-magnesium phosphate salt, 5.00 wt. % lauroylhydroxyproline, 8.00 wt. % water-soluble collagen (1% aqueous solution), 7.00 wt. % 1,3-butylene glycol, 7.00 wt. % ethanol, and the balance of purified water, and then a pack was prepared.

The particular examples, etc. of the present specification have been described in detail. It will be apparent to those persons skilled in the art that such detailed description is just preferred embodiments, and the scope of the present specification is not limited thereto. Accordingly, please note that the substantive scope of the present specification is defined by the claims attached herewith and equivalents thereof.

The invention claimed is:

1. A method for skin whitening comprising administering a compound of following formula 1, an optical isomer thereof, a pharmaceutically acceptable salt thereof, a hydrate thereof, a solvate thereof, or an extract of post-fermented tea comprising the same to a subject in need thereof:

[Formula 1]

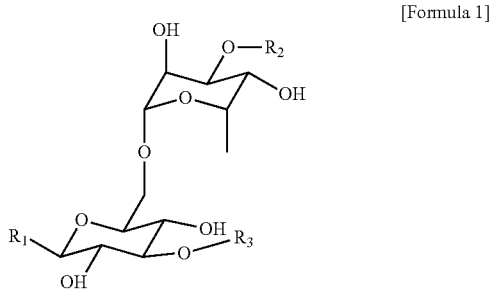

wherein in formula 1, $R_1$ is $C_{15}H_9O_7$, $R_2$ is H or $C_6H_{11}O_5$, and $R_3$ is $C_9H_7O_2$.

2. The method according to claim 1, wherein $R_1$ is represented by following formula 2:

[Formula 2]

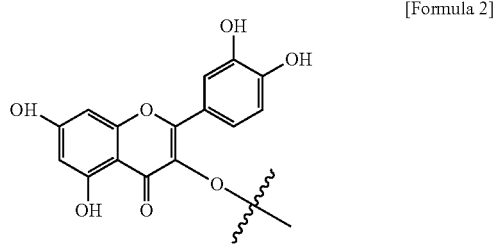 [SMILES: *Oc1c(-c2ccc(O)c(O)c2)oc2cc(O)cc(O)c2c1=O]

3. The method according to claim 1, wherein $R_2$ is represented by following formula 3:

[Formula 3]

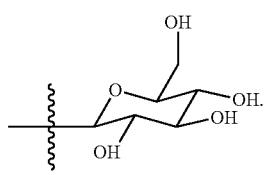

4. The method according to claim 1, wherein $R_3$ is represented by following formula 4:

[Formula 4]

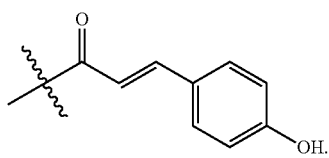

5. The method according to claim 1, wherein the compound is Quercetin3-O-[3-O"-(E)-p-coumaroyl][β-D-glucopyranosyl-(1→3)-O-α-L-rhamnopyranosyl-(1→6)-O-β-D-glucopyranoside].

6. The method according to claim 1, wherein the compound is quercetin3-O-[3-O"-(E)-p-Cumaroyl][α-L-Rhamnopyranosyl-(1→6)-O-β-D-Glucopyranoside].

7. The skin whitening composition according to claim 1, wherein the compound of the formula 1, the optical isomer thereof, the pharmaceutically acceptable salt thereof, the hydrate thereof, the solvate thereof, or the extract of post-fermented tea comprising the same inhibits one or more of tyrosinase activity and melanogenesis.

8. The method according to claim 1, wherein the compound of the formula 1, the optical isomer thereof, the pharmaceutically acceptable salt thereof, the hydrate thereof, the solvate thereof, or the extract of post-fermented tea comprising the same improves or treats one or more selected from the group consisting of freckle, ephelides, lentigo, birthmark, Melanoma, pigmentation caused by ultraviolet rays, pigmentation caused by drugs, pigmentation after inflammation, and pigmentation occurring in dermatitis.

9. The method according to claim 1, wherein:
the compound of the formula 1, the optical isomer thereof, the pharmaceutically acceptable salt thereof, the hydrate thereof, or the solvate thereof is administered in a form of a composition, and
the amount of the compound of formula 1, the optical isomer thereof, the pharmaceutically acceptable salt thereof, the hydrate thereof, or the solvate thereof in the composition is 0.00001 wt. % to 10 wt. %, relative to the total weight of the composition.

10. The method according to claim 1, wherein:
the extract of post-fermented tea is administered in a form of a composition, and
the amount of the extract of post-fermented tea in the composition is 0.1 wt. % to 90 wt. %, relative to the total weight of the composition.

11. The method according to claim 1, wherein the extract comprises the compound of formula 1, the optical isomer thereof, the pharmaceutically acceptable salt thereof, the hydrate thereof, or the solvate thereof in the amount of 0.00001 wt. % to 20 wt. %, relative to the total weight of the extract.

12. The method according to claim 1, wherein the dosage of the compound of formula 1, the optical isomer thereof, the pharmaceutically acceptable salt thereof, the hydrate thereof, or the solvate thereof is 0.00001 mg/kg/day to 100 mg/kg/day.

13. The method according to claim 1, wherein:
the compound of formula 1, the optical isomer thereof, the pharmaceutically acceptable salt thereof, the hydrate thereof, the solvate thereof, or the extract of post-fermented tea comprising the same is administered in form of a composition, and
the composition is a food composition, a cosmetic composition, or a pharmaceutical composition.

* * * * *